United States Patent [19]

Osther

[11] Patent Number: 4,816,387
[45] Date of Patent: Mar. 28, 1989

[54] METHOD FOR DETECTION OF ANTIBODIES TO HTLV-III AND DIAGNOSTIC TEST KIT USEFUL THEREWITH

[75] Inventor: Kurt B. Osther, Dallas, Tex.

[73] Assignee: Bio-Research Laboratories, Inc., Dallas, Tex.

[21] Appl. No.: 871,505

[22] Filed: Jun. 6, 1986

[51] Int. Cl.$^4$ .............................................. C12Q 1/70
[52] U.S. Cl. .......................................... 435/5; 422/61; 435/7; 435/28; 435/239; 435/805; 435/810
[58] Field of Search ................. 435/5, 7, 28, 239, 805, 435/810; 422/61

[56] References Cited

U.S. PATENT DOCUMENTS

| | | | |
|---|---|---|---|
| 4,452,901 | 6/1984 | Gordon et al. | 435/7 |
| 4,520,113 | 5/1985 | Gallo et al. | |
| 4,629,783 | 12/1986 | Cosand | 530/324 |
| 4,661,445 | 4/1987 | Saxinger et al. | 435/7 |

OTHER PUBLICATIONS

R. Gallo et al., Frequent Detection and Isolation of Cytopathic Retroviruses (HTLV-III) from Patients with AIDS and at Risk for AIDS, Science 224, 500–503, May 4, 1984.
J. Carlson et al., AIDS Serology Testing in Low-and High-Risk Groups, JAMA 253, 3405–3408, Jun. 21, 1985.
S. Weiss et al., Screening Test for HTLV-III (AIDS Agent) Antibodies, JAMA 253, 221–225, Jan. 11, 1985.
J. Schüpbach et al., Antibodies to HTLV-III in Swiss Patients with AIDS and pre-AIDS in Groups at Risk for AIDS, N. Engl. J. Med. 312, 265–270, Jan. 31, 1985.
G. Biberfeld et al., Antibodies to Human T Lymphotropic Virus Type III Demonstrated by a Dot Immunobinding Assay, Scand. J. Immunol. 21, 289–292, 1985.
V. Tsang et al., Enzyme-Linked Immunoelectrotransfer Blot Techniques (EITB) for Studying the Specificities of Antigens and Antibodies Separated by Gel Electrophoresis, Method in Enzymology 92, 377–391, 1983 Academic Press.
Towbin et al., "Electrophoretic transfer of proteins from polyacrylamide gels to nitrocellulose sheets: Procedure and some applications" Proc. Nat'l Acad. Sci. U.S.A. 76:4350–4354 (1979).
Groopman et al., "Serological Characterization of HTLV-III Infection in AIDS and Related Disorders" J. Infec. Dis. 153:736–742 (Apr. 1986).
Geroldi et al., "Western Blot Technique in the Serological Evaluation of Three LAV/HTLV III-infected Italian Families" Infection: 60–63 (1986).
Safai et al., "Seroepidemiological Studies of Human T-Lymphotropic Retrovirus Type III in Aquired Immunodeficiency Syndrome" Lancet I: 1438–1440 (Jun. 30, 1984).
Cabradilla et al., "Serodiagnosis of Antibodies to the Human AIDS Retrovirus with a Bacterially Synthesized env Polypeptide" Bio/Technology 4:128–133 (Feb. 1986).

*Primary Examiner*—Christine M. Nucker
*Attorney, Agent, or Firm*—Bryan, Cave, McPheeters & McRoberts

[57] ABSTRACT

The invention relates to a rapid and sensitive assay method for the detection of antibodies to Human T-Cell Leukemia Virus-III (HTLV-III), the AIDS virus, and diagnostic test kits for carrying out the method of the invention. According to the method of the invention, which is referred to as a Quick Western Blot, test samples and viral lysate are used in at least 50% greater concentrations than those used in conventional Western Blot techniques. In accordance with the invention, test results may be obtained in under two hours.

17 Claims, No Drawings

METHOD FOR DETECTION OF ANTIBODIES TO HTLV-III AND DIAGNOSTIC TEST KIT USEFUL THEREWITH

TECHNICAL FIELD

The present invention relates to a rapid and sensitive assay method for the detection of antibodies to Human T-Cell Leukemia Virus-III (HTLV-III) antigen, and diagnostic test kits for carrying out the assay method.

BACKGROUND OF THE INVENTION

Acquired immune deficiency syndrome (AIDS) was first recognized in approximately 1981, but the causative agent had not yet been identified. Intense research efforts resulted in the detection and isolation of HTLV-III, the retrovirus identified as the etiologic agent of AIDS.

The virus is currently believed to be transmitted through intimate sexual contact and blood. Thus far, epidemiologic evidence indicates that food, water, insects and casual contact are not disease vectors.

The AIDS virus acts by crippling the body's immune system. Particularly, HTLV-III selectively attacks $T_4$ lymphocytes, one of the subpopulations of lymphocytes that constitute the immune system. Infection with HTLV-III results in both a reduction in the number and a change in the function of the targeted $T_4$ lymphocytes with the eventual collapse of the immune system.

The groups at highest risk of infection with HTLV-III include homosexual and bisexual men and abusers of injected drugs. Other predictable high risk groups are women artificially inseminated with sperm from infected donors and sexual partners of those in the AIDS risk groups. Recipients of blood transfusions and blood products are also at risk of contracting AIDS.

Organ transplant recipients are also a high risk group. Recognizing organ transplantation as a potential avenue for the spread of AIDS, testing for HTLV-III antibodies is now performed on all organ donors. With the exception of some kidney transplants it is often difficult to predict in advance the source of a donated organ. For example, victims of fatal automobile accidents are potential organ donors, and as the time and place of accidents are not foreseeable, pre-transplant testing presents a problem. Screening is thus difficult in this and similar situations and the need for 24 hour testing facilities and, more importantly, on site testing is apparent. Further, in view of the limited useful life of a donated organ once removed from the host, the need for a rapid assay method is evident.

Present methods for the detection of antibodies to the AIDS virus include the enzyme-linked immunosorbance assay (ELISA), Western Blot and immunofluorescent techniques. Such assays are described in Sarngadharan, M.G. et al., Science 224:506 (1983) (ELISA); Tsang et al., In: Methods of Enzymology, Vol. 92, Chapter 29, 1983, Academic Press and Safai, B. et al., Lancet 1:1438 (1984) (Western Blot), and Essex, M. et al., Science 220:859 (1983) (immunofluorescent techniques). The established method for blood donor screening is to first carry out an ELISA, followed by confirmation of positives by Western Blot.

The ELISA technique involves reacting a test sample with an antigen reagent generally obtained from disrupted whole or density-banded HTLV-III. Typically, the HTLV-III is coated onto wells of a microtiter plate. After washing to remove unbound antibodies, goat-antihuman IgG antiserum conjugated with horseradish peroxidase is added to the wells and incubated. After an appropriate incubation period, an enzyme substrate is added to the mixture and a detectable, measurable color product is formed in the presence of antibodies to HTLV-III.

In the Western Blot technique, on the other hand, the HTLV-III antigen is electrophoretically resolved on SDS-polyacrylamide gels, each 8×10 cm gel being loaded with 5-10 μg of protein. The resulting protein bands are electro-transferred to nitrocellulose paper. Detection of antibodies to HTLV-III is then carried out by either solid phase strip radioimmunoassay techniques or by ELISA. Each of these methods includes an overnight incubation, and thus, an overall test time of about 20 hours.

The established screening procedure is not entirely satisfactory because of the time required to obtain results. This is particularly true in the organ transplant situation, especially for the heart and liver. These two organs have maximum cold ischemic times of 4 and 8 hours, respectively. Generally, ELISA takes about 4 hours and the Western Blot which, as noted, includes an overnight incubation period, requires about 20 hours. As can be appreciated, with conventional techniques test results would not be obtained within the maximum ischemic times for the heart or liver.

Accordingly, it is an object of the present invention to provide a rapid and sensitive assay for the detection of antibodies to HTLV-III whereby test results are obtained in under two hours, preferably before organ procurement is completed, but at least within the ischemic periods of the organs to be transplanted. It is a further object to provide diagnositc test kits for performing the assay method of the invention. Further objects and advantages of the present invention will become apparent upon reading the following description.

BRIEF DESCRIPTION OF THE INVENTION

The present invention involves a rapid and sensitive method for the detection of antibodies to HTLV-III antigen which combines modified Western Blot and ELISA techiques. The method of the invention applies blotting techniques but uses at least 50% more HTLV-III viral lysate than conventional Western Blot. In particular, from 13 to about 23 μg of HTLV-III antigen protein/8×10 cm gel is used in the method of the invention as compared with 5-10 μg of protein/8×10 cm gel used in conventional Western Blot. Concentrations of test sample are also increased at least 50% over that used in conventional Western Blot. The method of the invention, like the conventional Western Blot, employs an electrophoretically resolved antigen subsequently electrotransferred to test sheets or strips. According to the method of the invention, however, the antigen concentration of the lysate is increased from 130% to 460% of the lysate concentration used in the conventional Western Blot which together with the increased sample concentration facilitates a drastic reduction in incubation times. In accordance with the present method, test results are obtained in one hour and 20 minutes, that is 1/15 the time required to perform the conventional Western Blot. The method hereof is, therefore, referred to as a "Quick Western Blot" technique.

The amount of protein subjected to electrophoresis in the Western Blot assay is inversely related to the distinctiveness of the resulting bands, the potential for "noise" bands increasing with the amount of protein. Noise bands often appear adjacent to critical protein bands and may be mistaken therefor, making evaluation of test results difficult and increasing chances of false positives. It has, accordingly, previously been assumed that the use of relatively low antigen lysate concentrations, i.e., from about 50–10 μg of protein/8 × 10 cm gel, are necessary to facilitate accurate detection of antibodies to HTLV-III. Surprisingly, according to the present method, it has been found the accuracy of the present assay is excellent despite that the use of markedly increased antigen lysate concentrations together with an increased concentration of test sample. In fact, accuracy of the Quick Western Blot approximates that of the Western Blot notwithstanding the fact that the assay may be completed in 1/15 the time required for the conventional Western Blot.

In one preferred embodiment of the present invention, a diagnostic test kit is provided which permits on site testing for antibodies to AIDS virus. The diagnostic kit of the invention includes predeveloped positive and negative reference strips and reagent control strips for evaluating the test results by visual comparison with test strips. Accordingly, reading the results of the test is facilitated and the need for specially trained personnel is virtually eliminated. On site testing is particularly important in the organ transplant situation because screening for AIDS can now be performed on a 24 hour basis at virtually any location, without specially trained personnel, and test results can be obtained in 80 minutes, comfortably within the life span of ischemic organs.

DETAILED DESCRIPTION OF THE INVENTION

In accordance with the method of the invention, HTLV-III antigen concentrate is obtained and electrophoretically resolved. The HTLV-III antigen concentrate may be commercially obtained, for example, as from Litton Bionetics as HTLV-III viral lysate, Catalog no. 8464-15. The antigen concentrate is diluted in buffer to a protein concentration at least 50% greater than that utilized in conventional Western Blot. Preferably, the antigen concentrate is diluted in buffer to a protein concentration of 13–23 μg per 8 × 10 cm gel. The preferred buffer is 0.05 M TRIS-HCl/50% glycerol, pH8, 2.5% SDS (sodium dodecyl sulfate) and 5% mercaptoethanol. Other buffers known to those skilled in the art are also suitable, such as 9 M urea in 0.01 M TRIS-HCl. As noted above, the protein concentration of the antigen lysate used with the method of the invention is approximately 1.3 to as much as 4.6 times greater than the 5–10 μg/8 × 10 cm gel typically used for conventional Western Blot. See pages 380 to 381 of the guidelines published by Tsang V.C., J. Peralta, R. Simons, In: Methods of Enzymology, Vol. 92, Chapter 29, 1983, Academic Press Inc., which sets forth the 5–10μg/8 × 10 cm gel workable range of protein concentrations used in "conventional Western Blot" techiques.

A tracking dye is preferably added to the diluted antigen to produce visible protein banding. The preferred dye is bromophenol blue. The dye is preferably prepared by dissolving 50 mg bromophenol blue in 8 ml of glycerol, plus 1 ml each of 0.5 M TRIS-HCl at pH 8.0 and H$_2$O. Other dyes, as known to those skilled in the art, may also be used. After denaturation by boiling, typically for about 5 minutes, the antigen is subjected to conventional gel electrophoresis of the type reported by Tsang et al, Methods in Enzymology, Vol. 92 (1983).

Suitable gels for the electrophoresis are also prepared in accordance with the method of Tsang et al., Methods in Enzymology Vol. 92 (1983). A 10% polyacrylamide gel with a 3% stacking gel (SDS-PAGE) is preferred because it resolves a molecular weight range of 12,000–160,000, thus embracing the proteins within the HTLV-III viral lysate. However, a gradient SDS-PAGE gel can also be used. For example, a gradient ranging from 3.3%–20% polyacrylamide resolves the antigen in the desired molecular weight range. Preferably, a molecular weight marker is electrophoresed together with the HTLV-III antigen. These marker materials serve to calibrate the gels and facilitate identification of the protein bands of specific molecular weights. Suitable molecular weight markers are commercially available, such as a Cytochrome C molecular weight system from United States Biochemical Corporation.

Subsequent to electrophoresis, the protein bands of the resolved antigen are electro-transferred preferably to nitrocellulose sheets, (e.g., those commercially available from Schleicher and Schuell, Inc. as Item no. BA 83, which is a roll of nitrocellulose paper having a 0.2 micron pore size). Other types of papers, known to those skilled in the art, such as diazo paper are also suitable. The electro-transfer of the protein bands is accomplished by means of the technique reported by Tsang et al., Methods in Enzymology Vol. 92, particularly page 378, and W. Van Raamsdonk, et al, J. Immunol. Methods 17:337 (1977).

According to a preferred embodiment of the present invention, the nitrocellulose sheets are cut into strips approximately 2–2.5 mm in width. Each strip, after appropriate labelling, is placed in a separate test tube for determination of antibodies to HTLV-III viral lysate by the enzyme linked immunoassay of the invention. The nitrocellulose strips can also be placed in incubation trays for in house testing. It should be understood, however, that an uncut sheet can be placed in an incubation tray equipped with a pressing cover rather than cut into individual strips. This technique is also well-suited to in-house as opposed to on site testing. As can be appreciated, however, on-site testing is facilitated by use of individual tubes. Also, placing the strips in individual tubes minimizes the need for handling during the assay procedure and thus, possible smearing of the fragile protein patterns with fingerprints. Using strips is also more economical than uncut sheets because less reagent is necessary to carry out the test.

Test samples, positive and negative references and reagent controls are added to the tubes containing the nitrocellulose strips containing the resolved antigen. Test samples include, but are not limited to serum, semen and other body fluids. The positive reference is typically a sample known to contain antibodies to the HTLV-III viral lysate. Positive references have been obtained from the Centers for Disease Control (CDC), Atlanta, Georgia. Alternatively, a positive reference may be made from any sample which has been standardized with a positive reference obtained from the CDC. Standardization typically means that the same test results were obtained in about 20 runs. In accordance with the method of the invention, the positive reference is diluted 1:500 (1 part positive reference to 500 parts buffer) in PBS (phosphate buffered solution)-Tween, pH 7.2–7.4. Typically, 6 μl of the positive reference is mixed with 3 ml PBS-Tween.

The negative control is a sample known to be devoid of antibodies to HTLV-III viral lysate, and according to the method of the invention, is prepared by diluting 1:50 with PBS-Tween, pH 7.2–7.4. Typically, 60 μl of a negative reference is mixed with 3 ml PBS-Tween. Negative references have also been obtained from the CDC.

As the assay method of the invention is a qualitative rather than quantitative determination, the positive and negative references are used to evaluate the test results by comparison with the results obtained for test samples.

The reagent control is included as a quality control feature of the present invention and is used to assure accurate functioning of the test. Normally, the reagent control is the buffer used to dilute test samples and controls. Preferably, PBS-Teen, pH 7.2–7.4 is used as the reagent control.

According to the method of the invention, test samples are more concentrated than those used in conventional Western Blot, to accelerate the binding of antibodies to HTLV-III viral lysate to the antigen contained in the strips. Typically, test samples are at least 50% more concentrated than samples tested by conventional Western Blot techniques.

For serum samples, at least twice the concentration utilized in conventional Western Blot is required, i.e., a dilution of one part serum to 50 parts buffer as compared to a 1:100 dilution factor used in conventional Western Blot analysis. (See Tsang et al., Method of Enzymology, Vol. 92, 1983.) Theoretically, the actual dilution factor for particular samples may be varied, however, depending upon whether a specimen gives an extremely weak positive response. Studies indicate that four times the serum concentrations normally used with conventional Western Blot are unsuitable because the high amount of serum proteins, other than the antibodies being evaluated, interfere with the test. A PBS-Tween, pH 7.2–7.4 buffer is preferred for the dilution of samples. Typically, 60 μl of a serum sample is mixed with 3 ml of PBS-Tween. But other known buffers may be substituted.

The strips are then incubated with the positive and negative references, controls and test samples at room temperature, preferably for about 10 to 20 minutes, to permit the binding of any antibodies to HTLV-III present in the sample to the antigen in the nitrocellulose strips. A 20 minute incubation period is particularly preferred to insure optimum binding of weak positives.

The liquid content of each tube is discarded, with the strips remaining in place in the tubes. The strips are then washed, preferably with PBS-Tween buffer at pH 7.3. In particular the washing cycle includes four 1 minute washings with PBS-Tween. The strips are then incubated with an enzyme-conjugated anti-human IgG antiserum preferably for about 10 to 20 minutes, at room temperature, to permit binding of the enzyme conjugated antiserum to any antibody which bound to the antigen during the first incubation period. Preferably, goat anti-human IgG antiserum-horseradish peroxidase conjugate is employed, although other enzyme conjugated antisera as are known to those skilled in the art may be used. Again, a 20 minute incubation period is preferred.

Once more, the liquid content of each tube is discarded. The strips are then washed. Preferably the washing cycle includes four 1 minute washings with PBS-Tween followed by one 1 minute washing with PBS.

Then, the strips are incubated with an enzyme substrate for about 10 minutes at room temperature, for production of a color. The appropriate substrate for use with horseradish peroxidase enzyme is 3,3' diaminobenzidinetetrahydrochloride dihydrate (DAB). It should be understood, however, that substrate selection is dictated by the enzyme used. After the incubation period, the color reaction is stopped by addition of distilled $H_2O$ and the results determined, according to standard techniques, as reported by Tsang, et al., Methods in Enzymology, Vol. 92 (1983).

As can be appreciated, in accordance with the present invention, determination of the presence of antibodies to HTLV-III can be accomplished in less than 80 minutes because of the greatly reduced incubation times, totalling about 50 minutes, as compared with normal Western Blot which requires at least 20 hours.

In accordance with a preferred embodiment of the invention, a self-contained diagnostic test kit is provided which permits "on site" screening for antibodies to HTLV-III virus. The test kit includes a set of tubes containing positive and negative references and at least 1 buffer tube containing a predetermined volume of buffer to which the test sample is added in a predetermined amount to obtain a sample concentration of at least 50% greater than that utilized in conventional Western Blot techniques. The reference and control tubes are prediluted, and thus, the user need only dilute the test sample. A set of strip tubes is also provided, each tube containing a nitrocellulose strip containing resolved HTLV-III antigen protein, electrotransfered from an 8×10 cm SDS-PAGE gel loaded with at least 50% greater antigen protein concentration than that used in conventional Western Blot. Preferably, the strips contain resolved HTLV-III viral lysate, electrotransfered from an 8×10 cm SDS-PAGE gel loaded with from 13–23 μg of antigen protein. In a preferred embodiment, the reference, control and sample tubes are numbered. The strip tubes are assigned numbers corresponding to those on the reference control and sample tubes. The strips are assigned numbers corresponding to the tubes in which they are placed. This type of numbering systems avoids inadvertent mix ups which can destroy the accuracy of the assay. As can be appreciated, if the top of a tube containing a positive sample is placed on a tube containing a negative sample, it is likely to obtain a false positive result. Included in the kit are vials of enzyme-conjugated antiserum reagent, substrate or color change indicator, two washing buffers and solution for terminating the color reaction. Preferably, goat anti-human IgG antiserum-horseradish peroxidase is used as the enzyme conjugated anti-serum reagent. The preferred substrate, reaction terminating agent and washing buffers are DAB, distilled $H_2O$, and PBS Tween and PBS, respectively.

Preferably, pre-developed positive and negative reference strips and reagent control strips are provided in the kit. These controls, which serve the same purpose as described in connection with the method of the invention, are prepared in substantially the same manner as previously described except that after developing, the strips are air dried. The predeveloped strips are used to evaluate the test results by a visual comparison with the test strips after completion of a color reaction. The reagent control as noted, is provided to assure the accurate functioning of the reagents. The predeveloped reference and control strips are a significant feature of the present invention because they facilitate reading the assay results and practically eliminate the need for a skilled technician to evaluate the results.

Also, as the kit is self-contained, no laboratory equipment is needed. The advantages of such a kit are apparent, as it facilitates screening for HTLV-III antibodies at any time and virtually at any place, including remote geographic areas and those locations lacking a 24 hour testing facility. As aforementioned, this is of utmost importance in certain organ transplantation situations.

In a preferred embodiment, the method of the invention employing the diagnostic test kit hereof, is carried out as follows:

60 μl of a test sample, e.g., a test serum, is added to a sample tube containing a predetermined volume of the preferred buffer. The contents of the tube are manually mixed, as by turning the tube end-over-end about 5 times. The negative and positive references and reagent control as noted, are prediluted, but should also be mixed by turning the tube end-over-end. The contents of the tubes are then emptied into the strip tubes provided, mixed as described, and incubated at room temperature for about 20 minutes. The liquid content of the tube is poured off and discarded. The strips are washed with a first wash buffer. Preferably, the wash cycle consists of four 1 minute washings with PBS-Tween. Goat anti-human IgG antiserum-horseradish-peroxidase is then incubated with the strips at room temperature for a second twenty-minute period. The contents are mixed as described. After the incubation, the liquid is poured off and discarded and the strips washed. Preferably, the wash cycle includes four 1 minute washings with PBS tween, followed by 1 one minute wash with PBS. The substrate is then prepared, by dissolving the preferred powdered DAB provided in the kit with PBS containing 0.003% $H_2O_2$ also provided. The substrate is then added to each strip tube and incubated with the strips for 10 minutes. Again, the liquid is poured off, and distilled water is added to the strips to stop the enzyme-substrate color reaction. The test results are evaluated by comparing the test strips with the pre-developed positive, negative and reagent strips provided with the kit, and the assay is completed within 80 minutes of the initial treatment of the test sample.

It has been reported that with HTLV-III infection the major immune reactivity is directed to p41, a 41,000 molecular weight protein believed to be an envelope antigen of the virus. Thus, the p41 band is of critical significance in the present method. Also of importance is p24, a 24,000 molecular weight protein. Typically, the test is considered positive if activity is recorded at the p24 and p41 bands. Accordingly, proper resolution of the HTLV-III antigen lysate is vital. The amount of protein subjected to electrophoresis is related to the distinctiveness of the resulting bands. Obviously, it is desirable to obtain distinct banding at the critical points, particularly p41 and p24 with few or no noise bands.

Table I, below, summarizes the results of a study comparing the visible protein bands obtained with varying HTLV-III antigen lysate concentrations employing the Quick Western Blot assay of the invention and the conventional Western Blot assay as described in Tsang et al., Methods in Enzymology, Vol. 92 (1983). The Quick Western Blot assay was carried out as follows:

(1) HTLV-III antigen was electrophoretically resolved according to the technique of Tsang et al., Methods in Enzymology, Vol. 92 (1983). Each 8×10 cm gel was loaded with antigen protein varying from 1–30 μg/gel. A 10% polyacrylamide gel with 3% stacking gel was used.

(2) The resolved antigen was electrotransfered to nitrocellulose sheets according to the method of Tsang et al., Methods In Enzymology, Vol. 92 (1983) and cut into 2.5 mm strips which were placed into tubes.

(3) The references, control and test sera were prepared as follows: sera: 60 μl of each sample was mixed with 3 ml PBS-Tween; positive reference: 6 μl of positive reference plus 3 ml PBS-Tween; negative reference: 60 μl of negative reference plus 3 ml PBS-Tween; reagent control: 3 ml PBS-Tween.

(4) The strips were incubated at room temperature for 20 minutes with test sera, positive and negative references and reagent control.

(5) The liquid was poured off and discarded.

(6) 30 μl of goat anti-human IgG antiserum-horseradish peroxidase conjugate diluted with 15 ml PBS-Tween was added to the strips and incubated at room temperature for 20 minutes.

(7) 3 ml of DAB was added to the reaction mixture of step 6 and incubated at room temperature for 10 minutes.

(8) 5 ml of $H_2O$ was added to the reaction mixture of step 7 to terminate the color reaction.

(9) The results were evaluated by comparing the strips with predeveloped reference and control strips.

TABLE I

| CONCENTRATION OF ANTIGEN LYSATE | VISIBILITY OF PROTEIN BANDS WITH VARYING CONCENTRATIONS OF PROTEINS | | | | | | | | | | | |
|---|---|---|---|---|---|---|---|---|---|---|---|---|
| | PROTEIN BANDING | | | | | | | | | | | |
| μg protein per 8 × 10 cm gel | p18 | | p24 | | p35 | | p41 | | p55 | | p65 | |
| | WB | QWB | WB | QWB | WB | QWB | WB | QWB | WB | QWB | WB | QWB |
| 1 | — | — | — | — | — | — | — | — | — | — | — | — |
| 2 | — | — | — | — | — | — | — | — | — | — | — | — |
| 3 | — | — | — | — | — | — | — | — | — | — | — | — |
| 4 | — | — | — | — | — | — | — | — | — | — | — | — |
| 5 | — | — | — | — | — | — | — | — | — | — | — | — |
| 6 | — | — | — | — | — | — | — | — | — | — | — | — |
| 7 | — | — | (+) | — | — | — | — | — | — | — | — | — |
| 8 | — | — | (+) | — | (+) | — | (+) | — | (+) | — | (+) | — |
| 9 | (+) | — | + | — | + | — | + | — | + | — | + | — |
| 10 | + | — | (1)+ | — | + | — | (+)+ | — | 1+ | — | (1)+ | — |
| 11 | 1+ | — | 1+ | — | 1+ | — | 1+ | — | 1+ | — | 1+ | — |
| 12 | | — | (+) | | — | | — | | — | | — | |
| 13 | | — | + | | (+) | | (+) | | — | | — | |
| 14 | | (+) | + | | + | | + | | (+) | | — | |
| 15 | | + | + | | + | | + | | + | | (+) | |
| 16 | | + | + | | + | | + | | + | | + | |

TABLE I-continued
VISIBILITY OF PROTEIN BANDS WITH VARYING CONCENTRATIONS OF PROTEINS

| CONCENTRATION OF ANTIGEN LYSATE | PROTEIN BANDING | | | | | | | | | | | |
|---|---|---|---|---|---|---|---|---|---|---|---|---|
| μg protein | p18 | | p24 | | p35 | | p41 | | p55 | | p65 | |
| per 8 × 10 cm gel | WB | QWB | WB | QWB | WB | QWB | WB | QWB | WB | QWB | WB | QWB |
| 17 | | + | | + | | + | | + | | + | | + |
| 18 | | + | | + | | + | | + | | + | | + |
| 19 | | + | | + | | + | | + | | + | | + |
| 20 | | + | | + | | + | | + | | + | | + |
| 21 | | + | | + | | + | | + | | + | | 1+ |
| 22 | | + | | + | | 1+ | | 1+ | | 1+ | | 1+ |
| 23 | | + | | + | | 1+ | | 1+ | | 1+ | | 1+ |
| 24 | | 1+ | | 1+ | | 1+ | | 1+ | | 1+ | | 1+ |
| 25 | | 1+ | | 1+ | | 1+ | | 1+ | | 1+ | | 1+ |
| 30 | | 1+ | | 1+ | | 1+ | | 1+ | | 1+ | | 1+ |

1. [1] = an adjacent noise band
2. ( ) = faint banding
3. + = distinct band; — = no band
4. WB = Western Blot which was carried out according to the method of Tsang et al.
5. QWB = the Quick Western Blot method of the invention
6. Molecular weights of the protein bands are × 1000.

The results indicate that with 13–23 μg/ml of protein per 8×10 cm gel, distinct banding is obtained with reduced incubation times. As shown, at concentrations of 5–10 μg, those typically used in classic Western Blot analysis, no visible bands are obtained at the reduced incubation times of the present method. In contrast, when carrying out the conventional Western Blot, protein concentrations exceeding 10 μg/8×10 cm gel produces noise bands adjacent all of the protein bands typically analyzed.

In this study, the conventional Western Blot was not performed with protein concentrations greater than 11 μg of protein, because previous studies, the results of which are not presented here, demonstrated that at concentrations greater than 11 μg there were overwhelming noise bands.

In another study, the Quick Western Blot method of the present invention was compared with the conventional Western Blot and ELISA (enzyme-linked immunosorbent assay) for relative specificity, sensitivity, positive and negative predictive values (defined below) and test-times. The results are summarized in Table II below. One hundred twenty one serum samples were obtained from the Irwin Memorial Blood Bank, San Francisco, California, together with the results of their HTLV-III ELISA testing. Quick Western Blot and regular Western Blots were run on each of the one hundred twenty-one samples. As shown in Table II, the method of the present invention required about 1/15 the time required for conventional Western Blot and was substantially as accurate.

For purposes of this study the Quick Western Blot was carried out as described above in connection with Table I.

As is shown in Table II, the results demonstrate that the Quick Western Blot is as sensitive as the Western Blot and has comparable specificity.

Sensitivity and specificity are terms used to indicate the relative reliability of an assay procedure. As used herein, sensitivity was calculated by dividing the number of true positives (TP), i.e., the presence of antibodies to HTLV-III viral lysate, by the sum of the true positives and false negatives (FN), i.e., samples containing antibodies to HTLV-III viral antigen but which tested negative. Specificity was calculated by dividing the number of true negatives (TN), i.e. samples containing no antibodies to HTLV-III viral lysate, by the sum of true negatives and false positives (FP), i.e. samples testing positive but which do not have antibodies to HTLV-III viral lysate.

The predictive value of any diagnostic test is important because it is also indicative of the accuracy and reliability of the technique. The positive predictive value is defined as the ability to predict the number of true positives, i.e., the presence of antibodies to HTLV-III viral lysate, as compared to the number of test positives. Positive predictive value is calculated by dividing the number of true positives (as determined by conventional Western Blot) by the sum of true and false positives. Negative predictive value is defined as the ability to predict the number of true negatives as compared to the number of test negatives. It is calculated by dividing the number of true negatives (as determined by Western Blot) by the sum of true and false negatives. As may be seen from Table II, the method of the invention has a 96.6% and 100% positive and negative predictive values, respectively.

The results of the study indicate that the Quick Western Blot is an accurate diagnostic tool which may be used with confidence in the detection of antibodies against HTLV-III.

The advantages of the Quick Western Blot are readily apparent. The presence of antibodies to HTLV-III can be detected in one hour and twenty minutes. The rapidity with which the test can be performed is enormously important to organ transplant recipients, since donated organs have a limited usable life span outside the body. Also, the diagnostic kit of the invention can be brought to the donor patient site. This is especially advantageous in geographic locations where no HTLV-III antibody testing facilities are available and in areas where there are no 24 hour facilities. Moreover, the diagnostic kits can be used in hospital or laboratory settings not otherwise equipped to perform such testing because the need for specialized equipment and specially trained personnel is eliminated.

TABLE II

COMPARISON OF QUICK WESTERN BLOT WITH ELISA AND CLASSIC WESTERN BLOT

| ASSAY METHOD | Specificity | Sensitivity | Positive Predictive Value[3] | Negative Predictive Value[3] | Test-Time In Hours |
|---|---|---|---|---|---|
| ELISA - HTLV-III Ab[2] | 99.6% | 98.3% | 33.1% | 99.9% | 2 |
| Classic Western Blot[1] | 100% | 100% | 100% | 100% | 20 |
| Quick Western Blot | 98.9% | 100% | 96.6% | 100% | 1.3 |

[1]Performed according to Tsang et al., Enzyme-linked immuno-electrotransfer techniques (EITB) for studying the specificities of antigens and antibodies, separated by gel electrophoresis. Methods Enzymol. 1983; 92:377-91. Western Blot is considered the standard.
[2]Abbott Laboratories HTLV-III Antibody ELISA testing was performed by the Irwin Memorial Blood Bank and the results kindly supplied along with the 121 serum samples.
[3]Positive predictive value = (TP/TP + FP); negative predictive value = (TN/TN + FN). (See accompanying text for explanation.)

Additionally, and apart from the organ donor situation, utilizing the method and diagnostic test kit of the invention hospitals can obtain fast and accurate results on patients suspected of HTLV-III infection, and thus expedite treatment. Moreover, if AIDS is diagnosed, hospital personnel can more readily adopt necessary precautions and minimize accidental viral contamination.

As discussed above, the current established screening method consists of first carrying out an ELISA test followed by confirmation of positives by Western Blot. In view of the short test time, high sensitivity, specificity and predictive values of the Quick Western Blot, it may be possible to eliminate the present cumbersome screening method altogether and perform just one diagnostic test - the Quick Western Blot.

While preferred embodiments of the invention have been described, it will be apparent to those of ordinary skill in the art that various changes and modifications may be made therein without departing from the spirit and scope of the invention. Accordingly, the above description should be construed as illustrative, and not in a limiting sense, the scope of the invention being defined by the following claims.

I claim:

1. A method for the detection of antibodies to Human T-Cell Leukemia Virus-III (HTLV-III), comprising, within 80 minutes,
   (a) contacting nitrocellulose paper containing blotted resolved HTLV-III antigen protein obtained from gel electrophoretically resolved HTLV-III viral lysate with a test sample, said antigen lysate being present in an amount at least 50% greater than 5-10 $\mu$g per 8×10 cm electrophoresis gel and the test sample being diluted no more than 1:50, to obtain thereby concentrations of antigen and test sample at least 50% greater than those used in the conventional Western blot assay and incubating the nitrocellulose paper and test sample to permit binding of antibodies present in the sample to the protein on the nitrocellulose paper;
   (b) contacting the incubated nitrocellulose paper of step (a) with an enzyme conjugated antiserum reactive with said antibodies, and incubating to permit binding of the antiserum to said antibodies;
   (c) contacting the incubated nitrocellulose paper of step (b) with an enzyme substrate specific for the enzyme of step (b), and incubating to thereby produce color;
   (d) stopping the color producing reaction of step (c); and
   (e) evaluating the amount of color produced as an indication of the presence of antibodies to HTLV-III viral lysate.

2. The method of claim 1, wherein said antigen lysate has a protein concentration of between 13-23 $\mu$g per 8×10 cm gel.

3. The method of claim 2, wherein said test sample is serum.

4. The method of claim 3, wherein said serum sample is diluted from 1:25 to 1:50 to obtain thereby a concentration of serum at least twice but less than 4 times greater than that utilized in the conventional Western Blot assay.

5. The method of claim 1 wherein the enzyme-conjugated antiserum is a goat-anti-human IgG-horseradish peroxidase.

6. The method of claim 5, wherein the substrate is 3,3' diaminobenzidinetetrahydrochloride dihydrate.

7. The method of claim 6, wherein the color producing reaction is stopped by addition of distilled water.

8. The method of claim 1, wherein the antigen lysate has a protein concentration of between 15-20 $\mu$g per 8×10 cm gel.

9. The method of claim 1, further comprising the steps of washing the nitrocellulose paper with buffers after incubation steps (a) and (b).

10. The method of claim 9, wherein the buffers are PBS-Tween, pH 7.2-7.4 and PBS.

11. The method of claim 1, wherein:
    (a) the nitrocellulose paper containing the blotted resolved HTLV-III antigen is incubated with the test sample for between 10 and 20 minutes;
    (b) the incubated nitrocellulose paper of step (a) is incubated with the enzyme conjugated antiserum for between 10 and 20 minutes; and
    (c) the incubated nitrocellulose paper of step (b) is incubated with the enzyme substrate for about 10 minutes.

12. A diagnostic test kit for the detection of AIDS specific antibodies comprising
    (a) a set of control tubes comprising positive and negative references;
    (b) at least one reagent control tube;
    (c) at least one dilution tube containing a predetermined volume of buffer for dilution of test samples no more than 1:50 to obtain a concentration of test sample of at least 50% greater than that used in the conventional Western Blot assay;

(d) a set of tubes containing nitrocellulose test strips containing resolved HTLV-III antigen, said antigen being obtained from gel electrophoretically resolved HTLV-III antigen lysate having a concentration of at least 50% greater than 5–10 $\mu g$ per $8\times 10$ cm gel to obtain a concentration of antigen of at least 50% greater than that used in the conventional Western Blot assay;

(e) enzyme conjugated antiserum;

(f) a color change indicator; and (g) predeveloped positive and negative reference strips and reagent control strips for evaluating the results of the test by visually comparing the predeveloped strips with the test-strips after completion of a color change reaction.

13. The diagnostic test kit of claim 9 wherein the enzyme conjugated antiserum is a goat-antihuman IgG-horseradish peroxidase.

14. The diagnostic test kit of claim 10 wherein the color change indicator is 3,3′ diaminobenzidinetetrahydrochloride dihydrate.

15. The diagnostic test kit of claim 9, further comprising at least two wash buffers.

16. The diagnostic test kit of claim 12 wherein said wash buffers are PBS-Tween and PBS.

17. The diagnostic test kit of claim 12 wherein the electrophoretically resolved antigen has a concentration of 13–23 $\mu g$ protein/$8\times 10$ cm gel.

* * * * *